(12) United States Patent
Honjo et al.

(10) Patent No.: US 7,414,171 B2
(45) Date of Patent: Aug. 19, 2008

(54) PD-1-LACKING MOUSE AND USE THEREOF

(75) Inventors: Tasuku Honjo, 19-4, Ohsagi-cho, Iwakura, Sakyo-ku, Kyoto (JP) 606-0001; Hiroyuki Nishimura, Boston, MA (US)

(73) Assignees: Ono Pharmaceutical Co., Ltd., Osaka (JP); Tasuku Honjo, Kyoto (JP)

( * ) Notice: Subject to any disclaimer, the term of this patent is extended or adjusted under 35 U.S.C. 154(b) by 311 days.

(21) Appl. No.: 10/416,798

(22) PCT Filed: Nov. 14, 2001

(86) PCT No.: PCT/JP01/09951

§ 371 (c)(1),
(2), (4) Date: Sep. 29, 2003

(87) PCT Pub. No.: WO02/39813

PCT Pub. Date: May 23, 2002

(65) Prior Publication Data

US 2004/0034881 A1 Feb. 19, 2004

(30) Foreign Application Priority Data

Nov. 15, 2000 (JP) .............................. 2000-347392

(51) Int. Cl.
*A01K 67/00* (2006.01)
*A01K 67/033* (2006.01)
*A01K 67/027* (2006.01)

(52) U.S. Cl. .............................. 800/18; 800/13; 800/14

(58) Field of Classification Search .................. 800/13, 800/18, 14
See application file for complete search history.

(56) References Cited

U.S. PATENT DOCUMENTS 5,629,204 A 5/1997 Honjo et al.

OTHER PUBLICATIONS

Nishimura et al., 1998, International Immunology, vol. 10, No. 10, pp. 1563-1572.*
Mogil et al., 1999, Pain, vol. 80, pp. 67-82.*
Sigmund, C., Jun. 2000, Arterioscler. Thromb. Vasc. Biol., p. 1425-1429.*
Wither et al., 1998, Journal of Immunology, vol. 161, p. 4555-4562.*
Leonard et al., 1995, Immunological Reviews, vol. 148, pp. 97-114.*
Rescher et al., 2004, Journal of Cell Science, vol. 117, p. 2631-2639.*
Nishimura, H. et al., Science, vol. 291, pp. 319 to 322, (2001).
Nishimura, H. et al., Immunity, vol. 11, pp. 141 to 151, (1999).
Nishimura, H. et al., J. Exp. Med., vol. 191 (5), pp. 891-897.
Nishimura., H. et al., International Immunology, vol. 10 (10), pp. 1563 to 1572, (1998).
Freeman, G. et al., J. Exp. Med., vol. 192 (7), pp. 1027 to 1034, (Oct. 2000).
Fazekas, G., et al., "Isolation and characterization of IGG-2A-reactive autoantibodies from influenza virus-infected BALB-C mice", European Journal of Immunology, vol. 20, No. 12, 1990, pp. 2719-2730.
Satoh, M., et al., "Pristane induces high titers of anti-Su and anti-nRNP/Sm autoantibodies in BALB/c mice Quantitation by antigen capture ELISAs based on monospecific human autoimmune sera," Journal of Immunological Methods, Eliesevier Science Publishers B.V., Amsterdam, NL, vol. 182, No. 1, May 11, 1995.
Bhavsar P.K., et al., "Isolation and characterization of the human cardiac troponin I gene (TNN13)", Genomics, Academic Press, San Diego, US, vol. 35, No. 1, 1996, pp. 11-23.
Crimando J., et al., "Characterization of murine brain-reactive monoclonal IgG autoantibodies," Brain Behavior and Immunity, vol. 9, No. 3, 1995, pp. 165-181.
Okazaki, Taku, et al., "Autoantibodies against cardiac troponin I are responsible for dilated cardiomyopathy in PD-1-deficient mice," Nature Medicine, Nature Publishing Group, New York, NY, US, vol. 9, No. 12, Dec. 2003, pp. 1477-1483.
Supplementary European Search Report dated Jun. 12, 2007, p. 1.
Luppi, Patrizia, et al., "Idiopathic Dilated Cardiomyopathy, A superantigen-driven autoimmune disease", Circulation, 1998, vol. 98, pp. 777-785.
Korean Office Action.

* cited by examiner

*Primary Examiner*—Shin-Lin Chen
(74) *Attorney, Agent, or Firm*—Sughrue Mion, PLLC

(57) ABSTRACT

The invention relates to BALB/c mice that are deficient in the programmed cell death-1 receptor (PD-1), a screening method for autoimmune disease medicine using these mice, an IgG self-reactive antibody that the mice produce, a protein that specifically reacts to the antibody and is produced in heart, and a diagnostic method for dilated cardiomyopathy using the protein. Because PD-1 deficient BALB/c mice spontaneously develop autoimmune disease, and specifically dilated cardiomyopathy, they are useful for screening for medicines against these diseases.

3 Claims, 5 Drawing Sheets

PD-1-LACKING MOUSE AND USE THEREOF

TECHNICAL FIELD OF THE INVENTION

The present invention relates to programmed cell death-1 receptor (hereafter, it is abbreviated as PD-1)-deficient BALB/c mice and the use. More particularly, it relates to PD-1 receptor-deficient BALB/c mice, a screening method of medicines against autoimmune disease by use of the mice, IgG self-reactivity antibody of which these mice produce specifically, a protein specifically reacted to the antibody and produced in heart and an diagnostic method in dilated cardiomyopathy by use of the protein.

BACKGROUND ART

Programmed cell death controlled embryologically or physiologically can be observed in all most tissues of various animals. Such programmed cell death is generally called, "Programmed cell death" or "Premeditated programmed cell death", and distinguished from "unexpected cell death" which could be caused by a pathologic mechanism.

First, PD-1 has been found in mice as a receptor that cells are related to process to premeditated programmed cell death through the activation (The EMBO J., vol. 11(11), 3887-3895 (1992); JP05-336973; EMBL/GenBank/DDJB Acc. No.X67914). Then, it has been found in human by using the gene of mouse PD-1 as a probe (Genomics 23:704 (1994); JP07-291996). Because PD-1 has expressed in lymphocytes with activation and has deeply related to autoimmune disease by researches of PD-1 deficient mice (International Immunology, Vol. 10(10), 1563-1572(1998); Immunity. Vol. 11, 141-151(1999)), it has been suggested to be used for treatments and diagnoses of decrease or accentuation of immune function, infectious disease, rejections in transplant and tumours, etc. Both mouse and human PD-1 are composed by 288 amino acids, and are type I membrane-bound 55 kDa proteins with the hydrophobic region in the penetrative area of the cell-membrane in the middle and the signal peptide (20 amino-acids) in the N-terminus. Deficient mice (called the knockout mice.) are indicated those which cannot produce the gene product in born by modifying a specific gene artificially, and are made to examine roles of factors and receptors that are the gene products.

However, dilated cardiomyopathy indicates the contractile dysfunction of left ventricle with the dilatation of left ventricular. Though 30% of patients considered to be dilated cardiomyopathy are assumed to be caused by inherent mutations in the structural gene to code the key component of heart muscle, which connects intracellular cytoskeleton with intercellular matrix, the remaining cases remain uncertain. In both cases, the disease is progress, and threatens the life, and there is no available treatment method excluding cardiac transplant now.

First, PD-1 deficient mice were made with C57BL/6 (Hereafter, omit it with B6) mice. It has been confirmed that PD-1 deficient C57BL/6 mice naturally developed so-called autoimmune disease such as lupus nephritis and arthritis, etc. (International Immunology, Vol. 10(10), 1563-1572(1998); Immunity. Vol. 11, 141-151(1999)).

However, it really has been not known to what influence the difference of the genetic background influences the loss of PD-1, in case that PD-1 is lacked in other strain mice.

DISCLOSURE OF THE INVENTION

The present invention relates to
1. A PD-1 receptor deficient BALB/c mouse,
2. A screening method of a medicine against autoimmune diseases, which comprises using the mouse of the preceding clause 1,
3. A screening method of the preceding clause 2 for autoimmune diseases caused by the production of an autoantibody,
4. A screening method of the preceding clause 2 in which the autoimmune disease is dilated cardiomyopathy,
5. An IgG self-reactivity antibody that the mouse in the preceding clause 1 specifically produces,
6. An about 33 kDa(33 kDa±5 kDa) that is specifically reacted to the IgG self-reactivity antibody of the preceding clause 5 and is produced in heart, specifically,
7. A diagnostic method in dilated cardiomyopathy, which comprises using the protein of the preceding clause 6,
8. A (gene) diagnostic method in dilated cardiomyopathy, which comprises detecting a gene that encodes the protein of the preceding clause 7.

Characteristics of the Mice of the Invention

PD-1 deficient BALB/c mice (written as PD-1(−/−)) started to die as early as 5 weeks of age, and by 30 weeks, two thirds of the mice had died. In normal BALB/c mice (written as PD-1(+/+)), such a symptom were not seen. Though the appearance of lupus nephritis and arthritis were seen in PD-1 deficient C57BL/6 (written as B6-PD-1(−/−)), these deaths of an initial stage were not seen.

As a result of the autopsy described later, PD-1(−/−) mice of the present invention was judged to develop dilated cardiomyopathy spontaneously and dead, because of the evaluation of the cardiac performance by the ultrasonography and the observations by the electron microscope and the fact of the immune response, etc.

It is thought that dilated cardiomyopathy of the autoimmune disease type was caused so that IgG1 subclass of autoimmunity antibody is produced and accumulates with combination with about 33 kDa of proteins produced in heart, specifically.

Aging C57BL/6-PD-1(−/−) mice are easy to develop lupus glomerulonephritis and arthritis, tempering with the fact without heart failures, it indicates that the dysfunction of PD-1 becomes potential diathesises of autoimmune diseases, and diseases of various types can be caused by combining the diathesis and the genetic background.

Like this, the possibility that the cause in dilated cardiomyopathy was an autoimmune disease by endogenous accommodation disorder that targets cardiac muscle, that is, the possibility not to have been proven up to now, was suggested.

BRIEF DESCRIPTION OF THE DRAWINGS

FIG. 2(A) shows LVDd (left ventricular end-diastolic size), (B) shows LVDS (left ventricular end-systolic dimension), (C) shows ventricular percent fraction shortening, and p indicates the value of t.

DETAILED DESCRIPTION OF THE INVENTION

Figure 1:
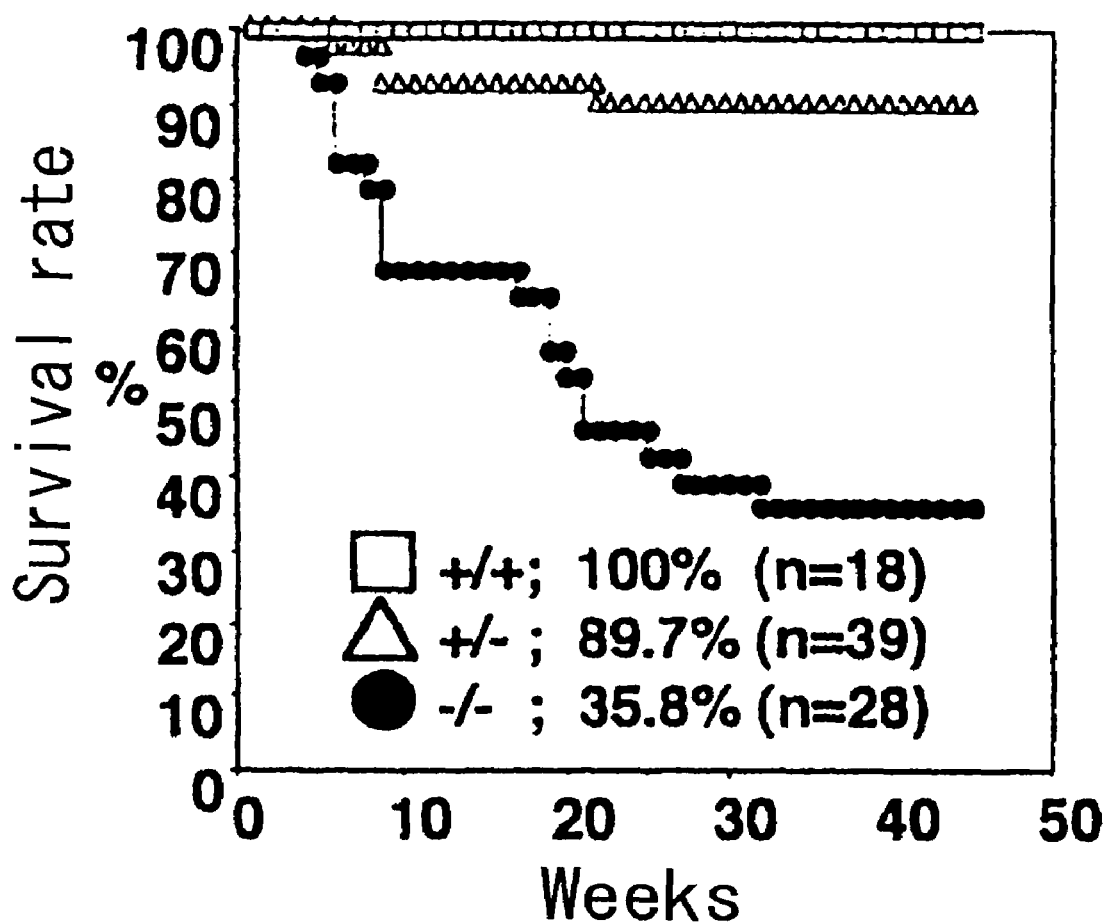
FIG. 1 shows survival curves of BALB/c-PD-1(−/−) mice (black circle), PD-1(+/−) mice (void triangle), and PD-1(+/+) (void square)(% shows these survival rates at 45 weeks of age, and values in parentheses shows the number of observed mice.).

1. Method of Acquiring Mice in the Present Invention

PD-1 receptor deficient BALB/c mice in the present invention are made by
(1) backcrossing PD-1 receptor-deficient C57BL/6(B6) mice with BALB/c mice tenth generation or more at least, or
(2) according to method described in International Immunology. Vol. 10(10), 1563-1572(1998), with embryo stroma (ES) cell lines from BALB/c mice.

For example, a targeting vector, which chromosome fragment (that which a part of exon was deleted, for example, fragment including exon 2-5 only.) including PD-1 gene, is inserted, is introduced into ES cell line from BALB/c mice, and the ES cell clone that the targeting vector caused the homology rearrangement at the position of PD-1 gene on the chromosome could be selected. BALB/c chimeric mice are made with PD-1 gene deficient ES cells, and PD-1 deficient BALB/c mice are made as the parents the chimeric mice that transmitted this deficiency to the germ line.

2. Screening

Medicines against autoimmune diseases, especially dilated cardiomyopathy could be screened by using PD-1 deficient BALB/c mice of the present invention. Moreover, they could be used on screening of medicines against autoimmune diseases that develop by production of autoantibody.

PD-1 deficient BALB/c mice of the present invention develop dilated cardiomyopathy and die. If the survival and the life prolongation are evaluated to the index after medicine is administered to PD-1 deficient mice, it is possible to be easy to screen it. Alternatively, by making the amount of autoantibody produced by the PD-1 deficient mice an index, medicines could be screened more efficiently. 3. IgG antibody produced by PD-1 deficient BLAB/c mice of the present invention, and about 33 kDa(33 kDa±5 kDa) of protein, which are recognized by the antibody and express in heart specifically.

In PD-1 deficient mice that develop dilated cardiomyopathy by aging, heart specific IgG antibody are recognized in blood and the deposition of IgG antibody in heart is confirmed. This IgG antibody specifically recognizes molecular weight about 33 kDa of the protein that expresses in heart. Though the production of this IgG antibody can be confirmed in mice that still does not develop dilated cardiomyopathy in PD-1 deficient mice, it was quantitatively low level ten fold or more.

The production of this IgG antibody is confirmed by neither wild type BALB/c mice nor PD-1 deficient B6 mice. Therefore, it is clear that this IgG antibody deeply relates to the development of dilated cardiomyopathy in PD-1 deficient BALB/c mice, it is thought to be produce under a specifically genetic background of BALB/c strain. Moreover, because PD-1 deficient B6 mice develop arthritis and nephritis that is so-called autoimmune disease, it indicates that the dysfunction of PD-1 becomes potential diathesis of autoimmune diseases, and can cause the disease of various types by combining the diathesis and the genetic background.

BEST MODE FOR CARRYING OUT THE INVENTION

Though, enumerating the example as follows, the present invention is explained more concretely, these do not limit the range of the present invention.

EXAMPLE 1

Making of PD-1 Deficient BALB/c Mice

PD-1 receptor deficient BALB/c mice written were made by backcrossing PD-1 receptor deficient C57BL/6(B6) mice with BALB/c mice tenth generation, according to method described in International Immunology. Vol. 10(10), 1563-1572(1998), with embryo stroma (ES) cell lines from BALB/c mice. Obtained mice were bred in facilities of the sterility.

EXAMPLE 2

Cause of Death of PD-1 Deficient BALB/c Mice

Breeding PD-1 deficient BALB/c mice (PD-1(−/−)) obtained in example 1, they started to die as early as 5 weeks of age, as black circles in FIG. 1 show. Then, by 30 weeks, two thirds of mice died. On the other hand, in normal BALB/c (PD-1(+/+)) mice (void squares in FIG. 1), which are not deficient of PD-1, those deaths were not observed. FIG. 1 shows with the result of breeding of PD-1 deficient (PD-1(+/−)) B6 mice.

PD-1(−/−) mice show the projection of the eyeball several days before death, and as a result of the autopsy, hearts in all mice were enlarged to anomalous. Moreover, tumefaction of livers were shown, and suggested that the cause of death was congestive heart failure.

EXAMPLE 3

Histological Examination

Histological examinations of dead PD-1 deficient BALB/c mice were done. Right ventricular walls of PD-1(−/−) mice were thinner than those of normal mice, and both ventricles were more enlarged to about two fold in diameter.

Though a sporadic fibrous react was observed including cellular interstitial fibrosis accompanied with scarring plasticand, ventricular walls appeared grossly normal. Electron microscopic examination revealed that throughout ventricular walls the scattered and disrupted myofilaments and the degeneration of cardiomyocytes with irregularly shaped mitochondria disarrayed. In atriums of large majority of mice, the thrombus seemed to depend on various sizes and almost huge congestion was observed.

EXAMPLE 4

Ultrasonic Echocardiography

Figure 2:
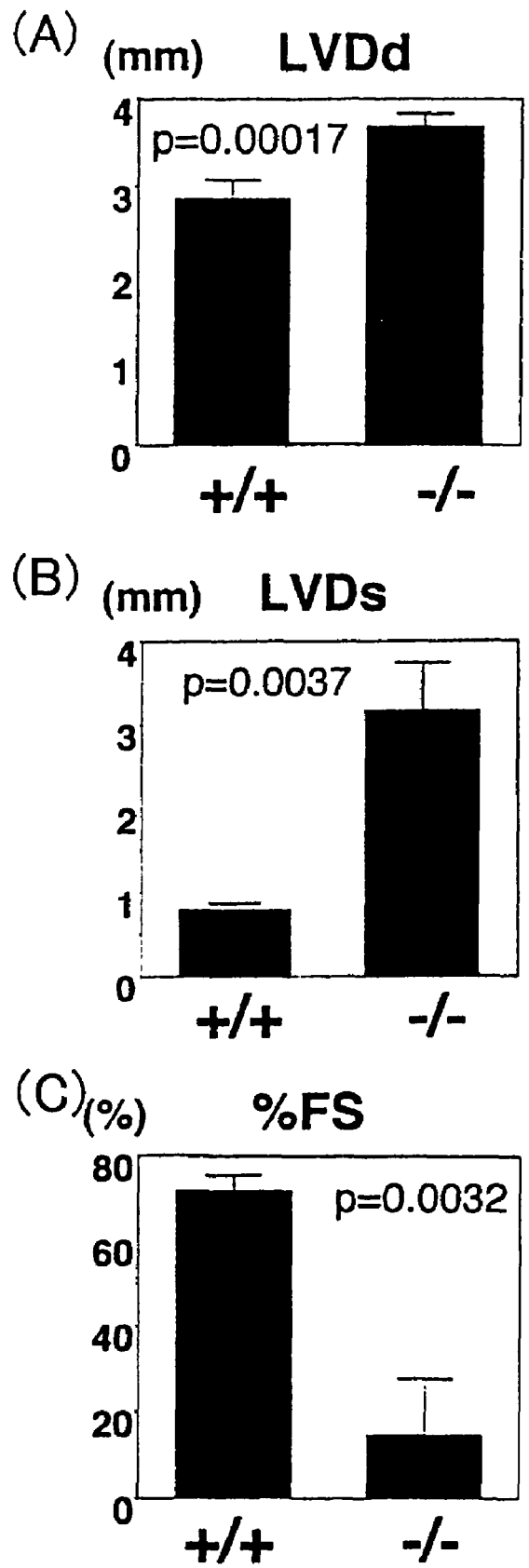
FIG. 2 shows results of transthoracic ultrasonic cardiography of PD-1(−/−) mice and normal (PD-1(+/+)).

To evaluate heart function on live, transthoracic echocardiography on PD-1(−/−) mice and normal (PD-1(+/+)) were done. The result is shown in FIG. 2(A) (LVDd:left ventricular end-diastolic dimension), (B) (LVDS:left ventricular end-systolic size) and (C)(ventricles fraction shortening %). Ventricular cavities of PD-1(−/−) mice, in particular those of right ventricles, appeared to greatly dilate, and their wall thickness were markedly reduced as compared with those of (PD-1 (+/+)) mice. The movement of left ventricle and interventricular septum was decreased at both diastole (LVDd) and systole (LVDs) in PD-1(−/−) mice (M-mode), and the ventricular fractional shortening, a measure of systolic function, was greatly reduced from 71.9% (PD-1(+/+)) to 14.9% (PD-1(−/−)).

This fact indicated that the pump function of PD-1 (−/−) mice heart was affected by dilation, and proved the diagnosis of dilated cardiomyopathy.

EXAMPLE 5

Immunotical Analysis

Because PD-1(−/−) mice bred on BALB/c-RAG-2(−/−) background has remained healthy, developments of heart disease in BALB/c-PD-1(−/−) mice have been attributed to the functions of immune responsive cells, therefore signs of heart-specific immune reactions were examined.

Immunofluorescent analysis revealed that linear depositions of IgG together with C3 complement surrounding the cardiomyocytes were detected in PD-1(−/−) mice hearts, whereas no significant IgG depositions were detected in PD-1 (+/+) mice hearts.

IgG depositions were diffusely observed throughout the entire cardiac wall. The linear dye patterns of IgG meant the binding of tissue specific autoantibody. On other organs, the depositions of IgG were hardly detected. The isotype of the deposited IgG was predominantly IgG1.

EXAMPLE 6

Autoimmune Response

To confirm the presence of autoimmune reactions to hearts, IgG autoantibody to normal heart extracts was examined by using serum of each mouse of BALB/c(n=4), BALB/c-PD-1 (+/−) (n=9) of which a heart was enlarged, BALB/c-PD-1 (−/−) (n=6) without development, B6(n=2), and B6-PD-1 (−/−) (n=5) for the presence of autoantibodies specific for heart tissue.

Figure 3:
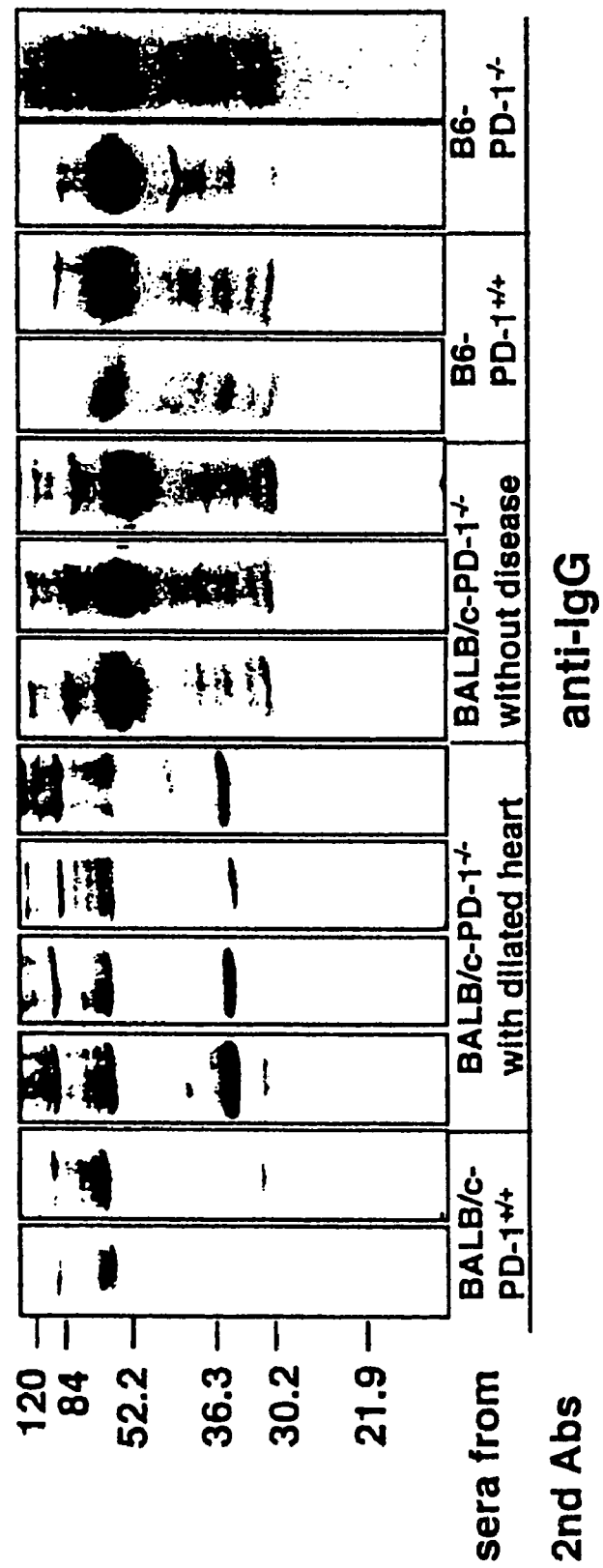
FIG. 3 shows electric patterns of IgG autoantibody to normal heart extract of each mouse sera of BALB/c(n=4), BALB/c-PD-1(−/−) (n=9) of which heart are enlarged, BALB/c-PD-1(−/−) (n=6) and B6(n=2) without development, and B6-PD-1(−/−) (n=5).

That is, extracts of normal hearts were made in a dissolution buffer (150 mM of sodium chloride, 25 mM of tris-hydrochloric acid buffer (pH 7.4), 5 mM of EDTA, 1% NP40 (protease inhibitor)) by using of the Polito Ron homogenizer. Lysate was subjected to electrophoresis in 12.5% SDS-PAGE, blotted onto filters, incubated with diluted serum, and was detected by biotinated anti-mouse IgG and streptavidin-armorachia rusticana peroxidase (the serum was continuously diluted to 30-300 fold.). FIG. 3 shows the result.

An autoantibody to 33 kD of protein was detected in all of 300 fold dilute serum of affected PD-1(−/−) mice, and almost of 1000 fold dilution, whereas such as autoantibody was not detected in 30 fold dilute that of PD-1 (+/+) mice.

An autoantibody was detected in 30 fold dilute serum of normal PD-1(−/−) mice and almost PD-1(+/−) mice, but not in more than 300 fold dilution.

Although a similar analysis was examined by using 7.5% SDS-PAGE within the range of high molecular weight, no signal more than background was detected.

As shown in FIG. 3, even in more than 300 fold dilutions of all serums obtained from nine PD-1(−/−) mice, high titer IgG that reacted with 33 kDa of protein in normal heart extract was detected.

Figure 4:
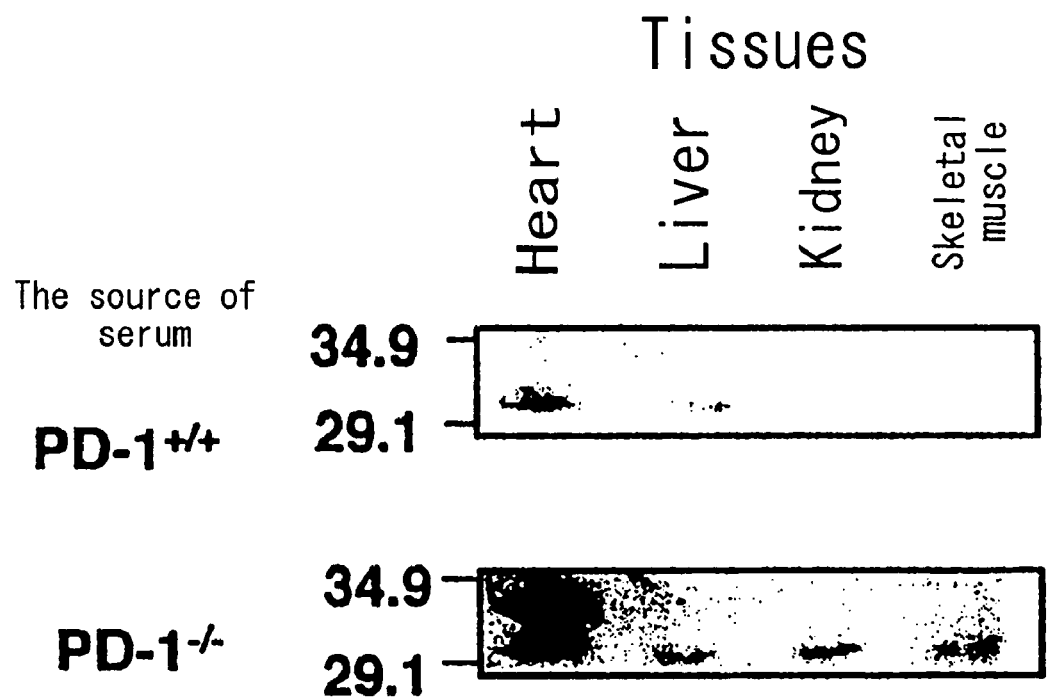
FIG. 4 shows immunoreactivities like FIG. 3 of serums from BALB/c and BALB/c-PD-1(−/−) mice of which weeks of age are corresponding, to the tissue extract of heart, liver, kidney, and skeletal muscle.

FIG. 4 shows immunoreactivities like FIG. 3 of serums from BALB/c and BALB/c-PD-1(−/−) mice that weeks of age are corresponding, to the tissue extract of heart, liver, kidney, and skeletal muscle. No autoantibody was detected even in 30 fold dilute serum of PD-1 (+/+) mice at the same weeks of age (zero of four).

The serum of PD-1(−/−) mice that did not presented hypertrophy with the macroscopic autopsy did not show enough reaction with 33 kDa of protein in the same 300 fold dilution (zero of six). Neither reaction detected in those of B6 or B6PD-1 (−/−).

However, when the density was raised, the former showed the reaction. Therefore, the existence of high titer IgG autoantibody to 33 kDa of protein completely correlated to a clinical symptom in dilated cardiomyopathy. Because 33 kDa of protein had not been detected in other tissues such as liver, kidney or skeletal muscle by the same serum from BALB/c PD-1 (−/−), it seemed that 33 kDa of autoantigen was specific for heart.

Figure 5:
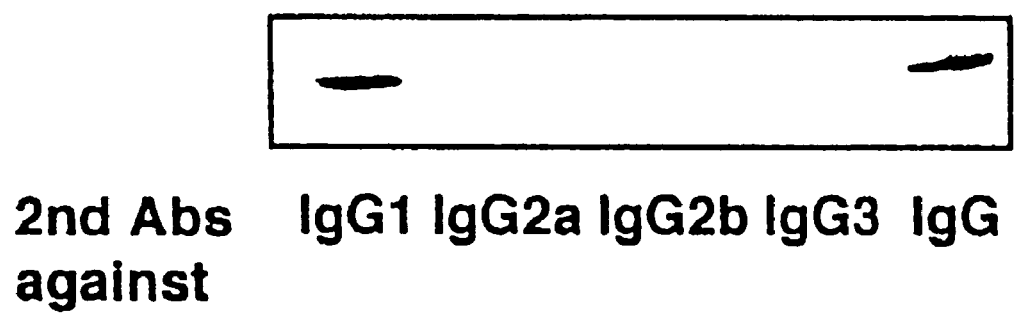
FIG. 5 shows the isotype of the serum autoantibody that recognizes 33 kDa antigen of heart in PD-1(−/−) mice.

No autoantibody including anti-dsDNA was detected in serum of PD-1(−/−) mice. Almost autoantibody was IgG1 classes in all of affected PD-1(−/−) mice (seven of seven), and proved the result of the immunostaining analysis of heart (FIG. 5: referring to the isotype of the serum autoantibody that recognizes 33 kDa of antigen from heart in PD-1 (−/−) mice).

Figure 6:
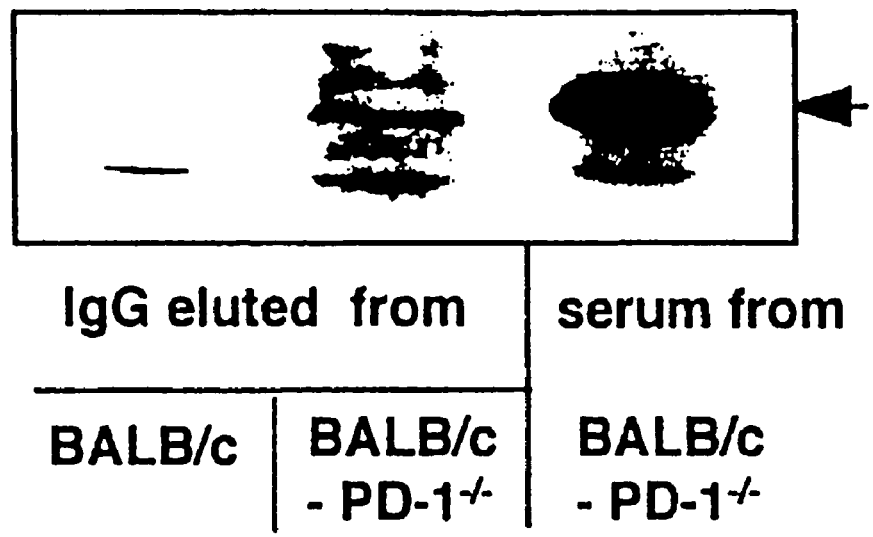
FIG. 6 shows the immunoreactivity to heart extract eluate of normal BALB/c and affected PD-1(−/−) mice and serum of PD-1(−/−) mice.

To analysis immunoreactivity of lysate together with serum of anagic PD-1(−/−) mice, tissue extracts were immunoprecipitated from normal heart extracts by protein G-beads, IgG deposited in heart of normal BALB/c and affected PD-1(−/−) were collected by acid elution, the reactivity examined directly. As shown in FIG. 6, far more a large amount of IgG was included in lysate from the PD-1 (−/−) mice compared with wild type BALB/c mice. Eluted IgG reacted with obviously specific 33 kDa of protein identified with that detected in serum of affect PD-1(−/−) mice. This result suggested that the circulating autoantibody could combine with the heart tissue in affected mice, specifically.

EXAMPLE 7

Transfusion to BALB/cRag-2(−/−) Mice

Splenic cells (20,000,000 pieces/mouse) from apparently normal PD-1(−/−) mice at 5 weeks of age were transfused to three BALB/c-Rag-2(−/−) mice through the vein. One mouse showed protrusion of eyeball 30 weeks after single injection. It was a typical dilated cardiomyopathy in the autopsy. In immunoblot with serum of this mice, the existence of IgG autoantibody to 33 kDa protein of the heart was shown by 1000 fold dilution.

EXAMPLE 8

Screening of Medicine Against Autoimmune Myocardiopathy

Medicines against autoimmune disease, especially dilated cardiomyopathy could be screened by using PD-1(−/−) mice obtained in example 1. Moreover, they could be used to screen medicines against autoimmune disease developed by production of autoantibody. PD-1 deficient BALB/c mice of the present invention develop dilated cardiomyopathy and die. If candidate compounds are administered to this PD-1 deficient mice, and evaluat the survival and the life prolongation as the index of the effect, they could be screened easily. Alternatively, autoantibody produced by this PD-1(−/−) mice can be measured by ELISA that uses the protein in claim 6. Therefore, medicines could be screened more efficiently by making the yield of the autoantibody an index.

REFERENCE EXAMPLE 1

Making of BALB/c-PD-1(−/−)-Rag-2(−/−)

BALB/c-PD-1(−/−) mice were returned to BALB/c-Rag-2 (−/−) mice, and thirty BALB/c-PD-1(−/−)-Rag-2(−/−) mice were created. These mice survive for forty-five days of the observation period, and symptoms of heart disease were not seen by the autopsy.

We claim:

1. A null mutant BALB/c mouse whose genome comprises null mutation on both programmed cell death-1 receptor (PD-1) alleles, wherein said mouse develops dilated cardiomyopathy.

2. The null mutant BALB/c mouse of claim 1, wherein said null mutant BALB/c mouse is obtained by backcrossing a PD-1 deficient C57BL/6 mouse with a BALB/c mouse for at least ten generations.

3. The null mutant BALB/c mouse of claim 1, wherein said null mutant BALB/c mouse produces IgG autoantibodies against a 33 kDa±5 kDa autoantigen specific to heart.

* * * * *